United States Patent [19]

Murase

[11] 4,286,590

[45] Sep. 1, 1981

[54] STACTOMETRIC APPARATUS

[75] Inventor: Masakazu Murase, Fujinomiya, Japan

[73] Assignee: Terumo Corporation, Tokyo, Japan

[21] Appl. No.: 58,932

[22] Filed: Jul. 19, 1979

[30] Foreign Application Priority Data

Jul. 24, 1978 [JP] Japan .................................. 53/90284

[51] Int. Cl.³ .......................... A61M 5/16; G05D 7/03
[52] U.S. Cl. ................................ 128/214 E; 128/771;
128/DIG. 13; 222/55; 222/63
[58] Field of Search .................... 128/214 E, 295, 771,
128/DIG. 13; 222/52, 55, 63, 76; 137/486,
487.5; 340/606, 609; 235/92 FL

[56] References Cited

U.S. PATENT DOCUMENTS

| 3,163,176 | 12/1964 | Darling | 137/487.5 |
| 3,656,478 | 4/1972 | Swersey | 128/214 E |
| 3,769,497 | 10/1973 | Frank | 235/92 FL |
| 4,037,598 | 7/1977 | Georgi | 128/214 E |
| 4,063,077 | 12/1977 | Wright | 235/92 FL X |
| 4,137,940 | 2/1979 | Faisandier | 137/486 |
| 4,181,130 | 1/1980 | Bailey | 128/214 E |

OTHER PUBLICATIONS

Montgomery Ward Catalog, "On Spring and Summer Stock", of 5/1978, p. 42, Mont. Ward, Chicago, IL 60607.

Primary Examiner—Charles N. Hart
Assistant Examiner—David R. Sadowski
Attorney, Agent, or Firm—Frishauf, Holtz, Goodman and Woodward

[57] ABSTRACT

A counter counts the time intervals of falling instilled drops in response to a signal issued each time a falling instilled drop is detected. A memory is supplied with data representing the quantities of a falling instilled drop corresponding to the time intervals at which the drops fall. The data corresponding to the time intervals thereof which have been counted by the counter are read out of the memory. The data thus read out are accumulated to determine the total quantities of the drops.

8 Claims, 5 Drawing Figures

STACTOMETRIC APPARATUS

BACKGROUND OF THE INVENTION

This invention relates to a stactometric apparatus for automatically measuring the amount of a medicinal solution to be instilled into the human body or a unit time amount of coeliac urine drawn off therefrom.

Measurement of a unit time amount of coeliac urine gives data on many physiological facts such as the circulatory function, the amount of a coeliac fluid, the metabolic function and the kidney function. Particularly, a unit time urine amount of 0.5 or 1 ml/hr kg (as measured per kg of the body weight of an examinee) is regarded as a very important indication in diagnosing the physiological condition of a patient. The above-mentioned data on the coeliac urine is effectively utilized in the early discovery and medical treatment of, for example, kidney insufficiency. The ureter is known to make a peristaltic motion in a brief period of time as 1 to 4 times per minute. On the other hand the kidney makes different actions during the daytime and nighttime; and further has its action intricately varied by the degree of metabolism or the amount of material resulting from the decomposition of cells or the level of blood pressure. One clue to the analysis of complicated relationships between the kidney function and the associated factors is to trace dynamic changes in the unit time quantity of coeliac urine. An attempt for the detailed analysis of the kidney function has made possible dialysis suited for a patient's physiological condition in medical treatment, for example, by an artifical kidney, thereby helping to elevate the function of the artificial kidney. Such attempt greatly assists in the early discovery and medical treatment of kidney diseases such as kidney insufficiency.

To date, the unit time quantity of coeliac urine has almost always been artificially measured. Namely, the coeliac urine has been conducted out of, for example, a patient's body through a urethral catheter to be measured per unit time by means of, for example, a messcylinder. Thus, the unit time quantity (ml/hr. kg) of coeliac urine has been calculated per kg of the body weight of a patient from the result of the measurement. Further, sometimes the unit time quantity of coeliac urine or the total amount thereof during a prescribed period of time has been recorded by means of an exclusive stactometric cylinder. However, the above-mentioned conventional coeliac urine-measuring process which involves the sampling of the urine, the measurement of its collected quantity and the calculation of the unit time urine quantity per kg of the body weight of a patient has involved a heavy work load on the analyzer. Further, the customary coeliac urine-measuring practice fails to be carried out automatically or continuously, and can not detect minute changes in the unit time quantity of coeliac urine. These difficulties make it impossible to fully indicate the unit time, quantity of a patient's coeliac urine, thus undesirably delaying the application of a proper medical treatment to the patient. Further, where a medicinal solution is instilled into the patient's body, the unit time quantity of the solution has been controlled simply by eye measurement, failing to correctly determine the unit time quantity of a medical solution being instilled.

SUMMARY OF THE INVENTION

This invention has been accomplished in view of the above-mentioned circumstances and is intended to provide a stactometric or stalagmometric apparatus which can automatically measure the unit time quantity of coeliac urine progressively accumulated in the body cavity or an instilled medicinal solution.

To attain the above-mentioned object, this invention provides a stactometric apparatus which comprises:

a device for measuring the lengths of time intervals at which drops of instilled material fall in succession;

a memory which stores data on the quantities of instilled drops corresponding to the different time intervals at which they fall; and means for reading from the memory the data on the quantities of instilled drops falling at the time intervals where lengths have been measured by the instillation time interval-measuring device.

DETAILED DESCRIPTION OF THE PREFERRED EMBODIMENTS

Figure 1:
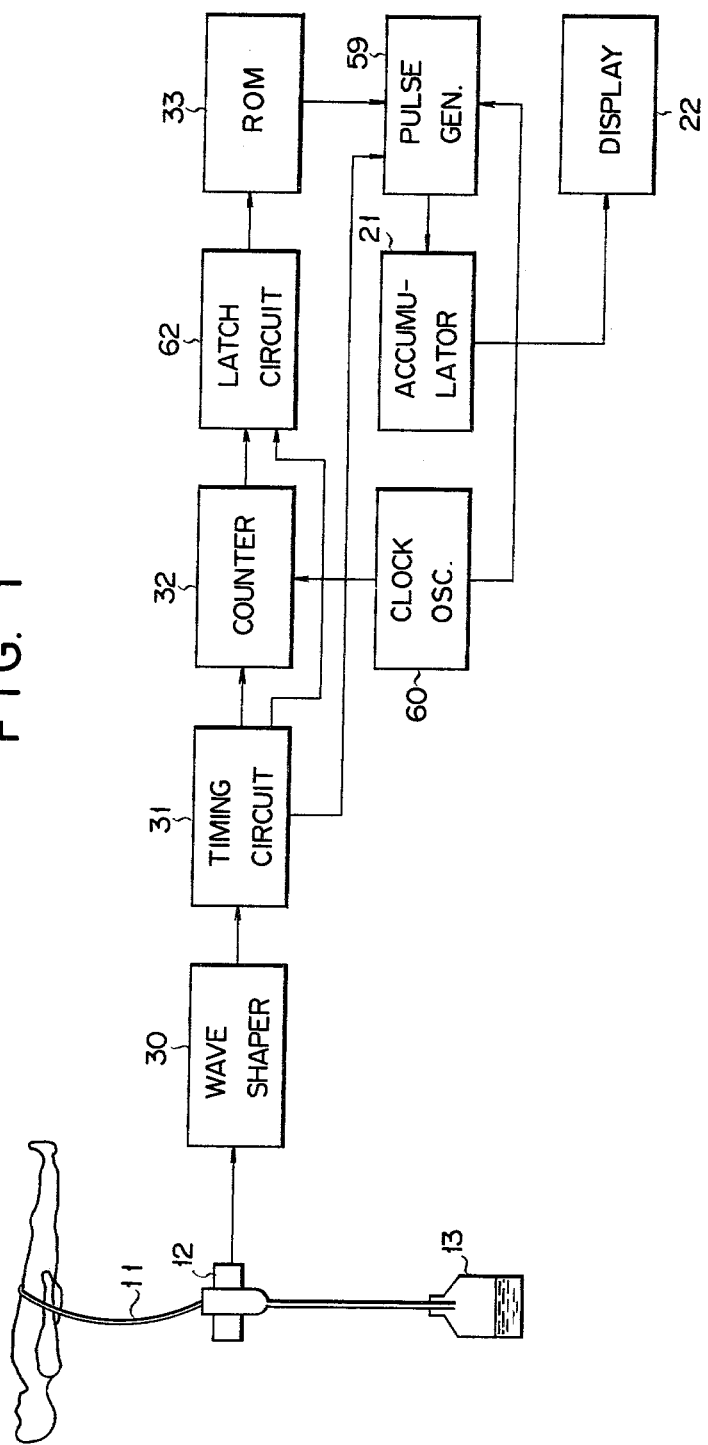
FIG. 1 is a block circuit diagram of a stactometric apparatus according to one embodiment of this invention which is used to measure the unit time quantity of coeliac urine progressively accumulated in the body cavity.
Figure 2:
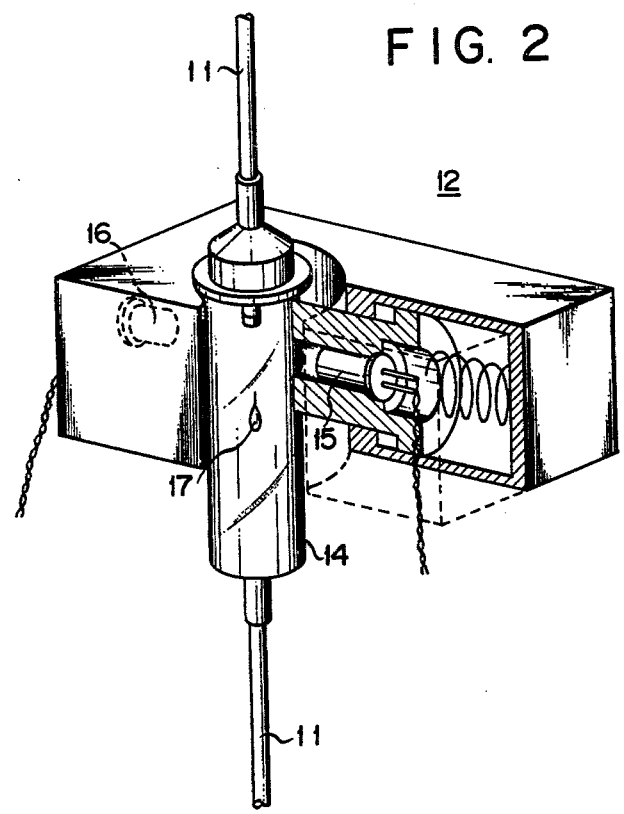
FIG. 2 is an oblique view, partly in section, of an instilled drop detector used with the stactometric apparatus of FIG. 1.

Referring to the embodiment of FIG. 1, a urethral catheter 11 extends from the human body to a urine receptacle 13 through a urine drop detector 12. This urine drop detector 12 is designed, as shown in FIG. 2, to photoelectrically detect a urine drop drawn off from the human body through the urethral catheter 11. This urethral catheter 11 is connected to the upper portion of an instillation cylinder 14, whose lower end is connected to the lower section of the urethral catheter 11. A light-emitting element 15 and a light-receiving element 16 are so positioned as to face each other through the instillation cylinder 14. The urine drop detector 2 generates an electric signal each time a urine drop 17 passes between the light-emitting element 15 and light-receiving element 16.

Figure 3:
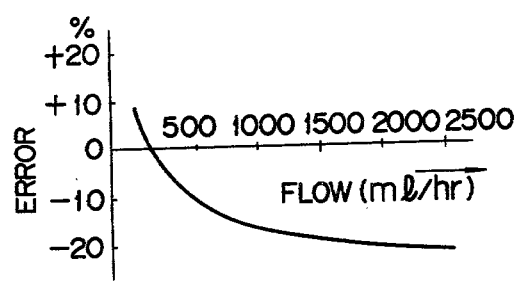
FIG. 3 graphically indicates the relationship between the time intervals of instillation and percentage errors occuring in measuring the quantities of material instilled at the time intervals.

An output electric signal from the urine drop detector 12 is supplied to a wave shaper 30 of FIG. 1. The wave shaper 30 is connected to a timing circuit 31 which generates a latch pulse and a reset pulse in response to the output pulse from the wave shaper 30. The interval between the latch and reset pulses is set at a sufficient lower value than the minimum interval of the urine drops. The reset pulse output terminal of the timing circuit 31 is connected to a counter 32, whose clock pulse input terminal is connected to a clock pulse oscillator 60 to receive clock pulses issued therefrom. The output terminal of the clock pulse counter 32 is connected to a latch circuit 62 which latches the contents of the counter 32 in response to the latch pulse from the timing circuit 31. The output terminal of the latch circuit 62 is connected to read only memory (ROM) 33. ROM 33 stores data on the different time intervals at which the respective urine drops fall. The time intervals vary with the quantities of the respective falling urine drops. If, therefore, an attempt is made to determine the quantity of coeliac urine drawn off, for example, from a patient's body for a given period of time by simply counting a number of urine drope falling during the period, then it is impossible to accurately measure the urine quantity. Examination was made of errors in measuring the urine quantities corresponding to the different intervals of falling urine drops with 15 urine drops assumed to measure 1 ml regardless of their sizes, the results being set forth in FIG. 3. As is apparent from FIG. 3, appreciably noticeable errors of measurement arose depending on the different lengths of the respective time intervals of falling urine drops.

For correction of the above-mentioned errors of measurement, the stactometric apparatus of this invention is provided with the ROM 33 which stores data on the quantities of urine drops corresponding to the different time intervals at which they fall.

An output signal read out of the ROM 33 is supplied to a pulse generator 59 as shown in FIG. 1, which generates a pulse signal having a number of pulses corresponding to the data read out of the ROM 33, in response to a timing pulse from the timing circuit 31. The pulses are conducted to an accumulator 21, an output signal from which is delivered to a display device 22 which indicates the quantities of urine drops totalled by the accumulator 21. A switch 23 is used to reset the accumulator 21.

Where, with the above-mentioned circuit arrangement, urine drops are drawn off from a human body to the urine drop detector 12 through a urethral catheter 11, then the urine drop detector 12 issues a pulse signal corresponding to the time interval at which the urine drops fall. The pulse signal is shaped by a wave shaper 30, and carried to a timing circuit 31. A clock pulse counter 32 counts clock pulses sent forth from a clock pulse generator 60. The count contents of the counter 32 are latched in the latch circuit 62 in response to the latch pulse from the timing circuit 31. The count contents latched in the latch circuit 62 represents the time interval at which the urine drops fall. After latching, the counter 32 is reset in response to the reset pulse of the timing circuit 31 to count the succeeding urine drop interval. The latched count contents specify the required address of the ROM 33. Data on the quantities of urine drops corresponding to the time intervals at which they fall are read out of the specified addresses of the ROM 33. Data on the quantity of a urine drop which has been read out of the specified address of the ROM 33 is converted by the pulse generator 59 into a pulse signal having a number of pulses corresponding to the quantity of the urine drop. The converted pulse signals are successively supplied to the accumulator 21 to be totalled. The quantities of urine drops accumulated by the accumulator 21 are shown on the display device, enabling the operator to easily recognize the unit time quantity of coeliac urine drawn off from the body of, for example, a patient.

As described above, the stactometric apparatus according to the foregoing embodiment of this invention automatically and continuously measures the unit time quantity of a patient's coeliac urine with the quantities of urine drops corrected according to the different time intervals at which they fall, thereby ensuring the accurate measurement of the quantity of a patient's coeliac urine collected for a given length of time.

There will now be described by reference to FIG. 4 a stactometric apparatus according to another embodiment of this invention. With this embodiment, the output terminal of the urine drop detector 12 is connected to a divider 34 through the wave shaper 30, timing circuit 31, clock pulse counter 32, latch circuit 62, ROM 33 and pulse generator 59 in turn. The timing circuit 31 is connected to the latch circuit 62 to determine the timing in which count contents of the counter 32 are to be latched in the latch circuit 62. The output terminal of the divider 34 is connected to a random access memory (RAM) 35. The output terminal of the RAM 35 is connected to a digital-analog (D/A) converter 38 through a pulse generator 36 and counter 37. The RAM 35 is connected to an address counter 39, whose address signal specifies the required address of the RAM 35. The divider 34 is connected to a weight data input device 40 comprising, for example, a sum rotary switch or keyboard which generates a signal denoting the body weight of, for example, a patient, and also to an accumulator 41 to have the quotients of division accumulated thereby. The output terminal of the accumulator 41 is connected to a digital-analog (D/A) converter 42. The output terminal of the pulse generator 36 is connected to an average amount counter 43. The output terminal of the ROM 33 is connected to a total amount counter 44. The output terminals of both counters 43, 44 are selectively connected to a display device 46 through the corresponding contacts of a changeover switch 45. The operations of the time counter 32, pulse generator 36, address counter 39, pulse generator 59, accumulator 41, and average amount counter 43 are controlled by a clock pulse issued from a clock pulse oscillator 47.

Figure 4:
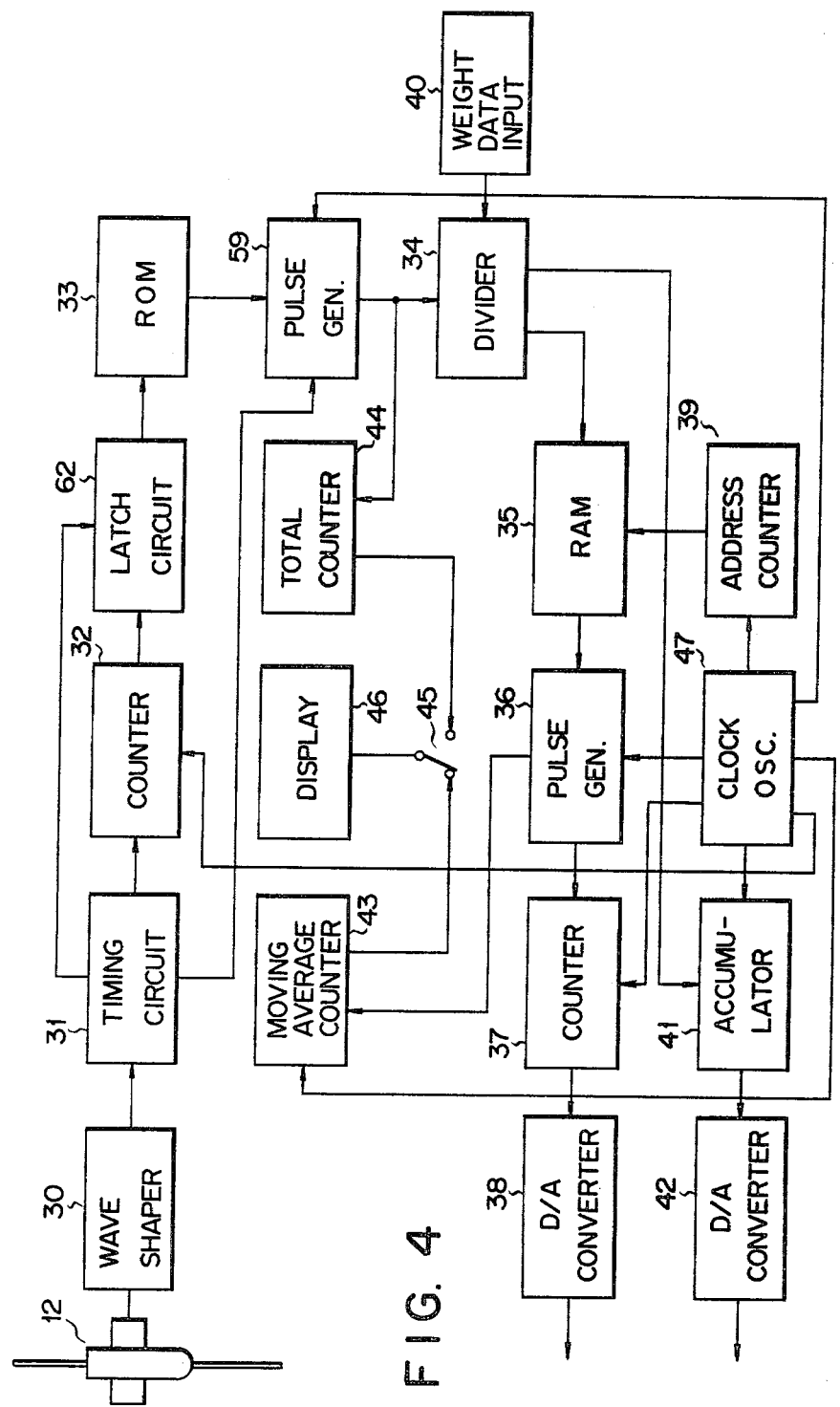
FIG. 4 shows the circuit arrangement of a stactometric apperatus according to another embodiment of the invention.

According to the circuit arrangement of a stactometric apparatus according to the second embodiment of FIG. 4, a pulse signal delivered from the urine drop detector 12 is shaped by the wave shaper 30, and conducted to the timing circuit 31. The clock pulse counter 32 measures the respective time intervals of the falling urine drops of a patient as the embodiment of FIG. 1. A count made by the counter 32 designates the required address of the ROM 33. Data on the quantity of a single urine drop corresponding to the count made by the time counter 32, that is, the time interval of a falling urine drop is read out of the specified address of the ROM 33. An output data on the quantity of a single urine drop which has been read out of the ROM 33 is converted by the pulse generator 59 into a pulse signal having a number of pulses corresponding to the quantity of a single urine drop, and carried to the divider 34. A unit time urine drop quantity is divided in the divider 34 by the body weight of a patient which is supplied from the weight input device 40 comprising, for example, a sum rotary switch or keyboard to determine the unit time urine drop quantity (ml/hr. kg) per unit body weight (kg). The unit time urine drop quantity supplied from the divider 34 is stored in the RAM 35. In this case, the respective unit time urine drop quantities are stored every 14 seconds in those addresses of the RAM 35 which are successively specified by address signals delivered from the address counter 39 operated in response to a clock pulse issued, for example, every 14 seconds from a clock pulse generator 47. Unit time urine drop quantity is read out of the RAM 35 whose addresses are successively supplied with data every 14 seconds in response to a signal from the address counter 39 which specifies the address from which data is to be read out. In this case, for example, 64 consecutive data on the unit time urine drop quantities stored in the RAM 35 (including the latest data) are read out. In other words, 64 consecutive data on the urine drop quantities collected every 14 seconds, that is, figures on the urine drop quantities collected during 15 minutes (14 seconds×64=896 seconds÷15 minutes) are read out. Urine drop quantities collected during the above-mentioned 15 minutes are read out every 14 seconds, that is, each time the latest data on the quantity of a urine drop is supplied. Figures thus read out of the RAM 35 respectively represent a moving average of the urine drop quantities collected during 15 minutes. Respective figures on the moving average of urine drop quantities are converted into a pulse signal by the pulse generator 36 and supplied to the digital counter 37, which digitally determines the moving average of urine drop quantity from the pulse signals received. A count made by the digital counter 37 is converted into an analog signal by a digital-analog (D/A) converter, which produces an analog signal representing the moving average of urine drop quantities.

Signals denoting the urine drop quantities per unit body of weight of, for example, a patient which are supplied from the divider 34 are conducted to the accumulator 41 to be successively added. Output accumulated data from the accumulator 41 is converted into an analog signal by the digital-analog (D/A) converter 42. Output pulses from the pulse generator 36 are counted by the average amount counter 43, and signals denoting the quantities of urine drops which are read out of the ROM 33 are counted by the total amount counter 44. Data on the moving average of urine drop quantities delivered from the average amount counter 43 and data on the total amount of urine drop quantities supplied from the total amount counter 44 are selectively supplied to the display device 46 by the action of the changeover switch 45.

The stactometric apparatus according to the second embodiment of FIG. 4 for determining urine drop quantities continuously indicate correct data on the moving average of urine drop quantities and the total amount thereof, thereby making it possible to correctly judge the affected condition of a patient.

The time interval at which urine drop quantities are collected to determine a moving average thereof can be freely varied by changing a number of figures on the urine quantities which are to be read out of the RAM 35.

The foregoing two embodiments relate to a stactometric apparatus for determining the unit time quantity of, for example, a patient's coeliac urine. However, this invention is also applicable to a stactometric apparatus for determining the instilled quantity of a medicinal solution.

There will now be described by reference to FIG. 5 the arrangement and operation of a stactometric apparatus for determining the instilled quantity of a medicinal solution. A medicinal solution-instilling catheter 51 connected to an instillation cylinder 50a of an instilled drop detector 50 is fitted to the human body to instill a medicinal solution thereinto. The output terminal of the instilled drop detector 50 is connected to the ROM 33 through the wave shaper 30, timing circuit 31, clock pulse counter 32, and latch circuit 62 in turn. The ROM 33 stores data on the quantities of the instilled drops of a medicinal solution corresponding to the different time intervals at which the drops fall. The output terminal of the ROM 33 is connected to an arithmetic circuit 55.

Figure 5:
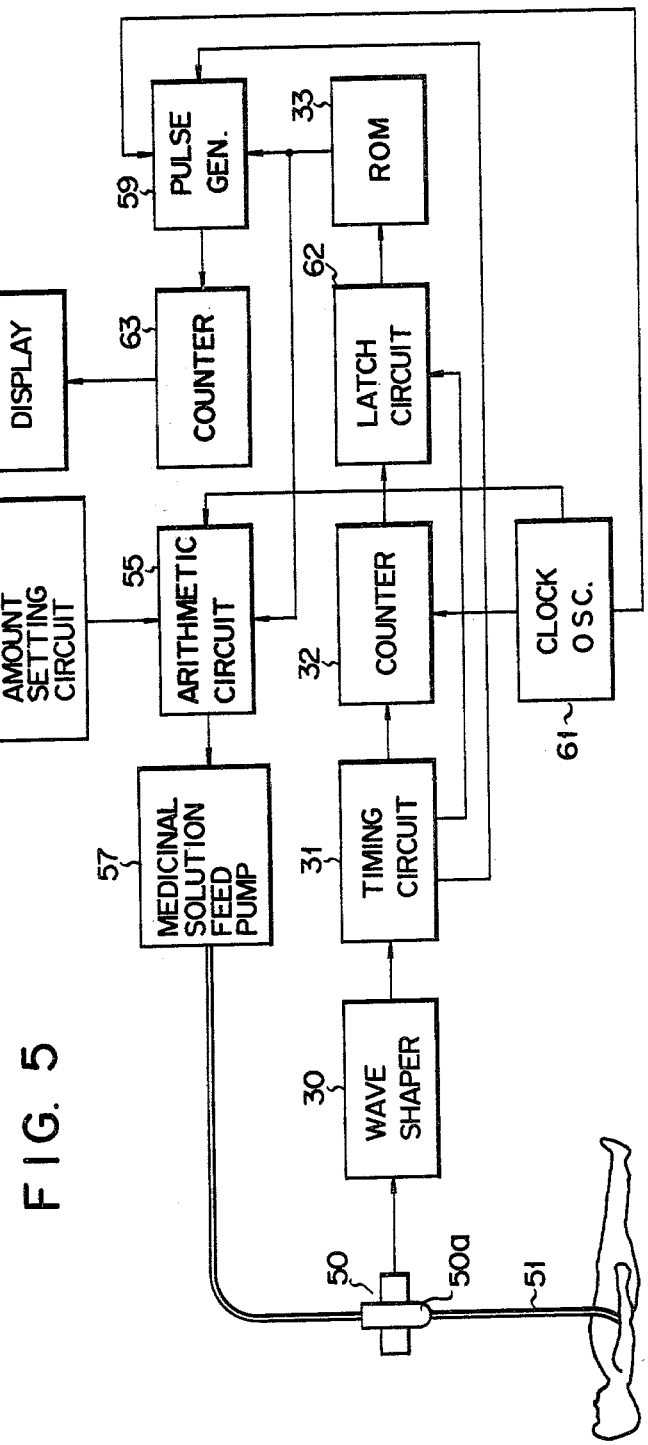
FIG. 5 indicates the circuit arrangement of a stactometric apparatus according to still another embodiment of the invention, which is used to instill a medicinal solution.

With the stactometric apparatus of FIG. 5, an instilled drop signal delivered from the instilled drop detector 50 is shaped by the wave shaper 30 and carried to the counter 32. This counter 32 counts a time interval at which an instilled medicinal solution drop falls in response to a timing signal and clock pulse.

The count contents of the counter 32 is latched in a latch circuit 62 and supplied as an address signal to the ROM 33 therefrom. An amount of a medicinal solution being instilled, which is defined by the address signal is read out of the ROM 33, and then supplied to the arithmetic circuit 55. The arithmetic circuit 55 calculates a proper amount of a medicinal solution being instilled, on the basis of equation: $F=(k/T\times f(T)$, where F expresses a proper amount of a medicinal solution, f(T) a function of readout data from the ROM, T a time interval of the instilled medicinal solution drops, and k constant. Comparison is made in the arithmetic circuit 55 between the proper amount (F) of a medicinal solution and the amount of a medicinal solution which has previously been defined by the instillation amount-setting circuit 56. The arithmetic circuit 55 issues an output signal corresponding to the excess or deficiency of the instilled amount of the medicinal solution. An output signal from the arithmetic circuit 55 controls the operation of a medicinal solution feed pump 57, thereby causing a proper amount of a medicinal solution to be supplied to the instillation cylinder 50a. An instillation amount thus determined is in an instillation amount counter 63 connected to the ROM 33 through a pulse generator 59, and is indicated on a display device 58.

The stactometric apparatus according to the embodiment of FIG. 5 always ensures the instillation of a proper amount of a medicinal solution and the satisfactory medical treatment of a patient.

As mentioned above, the stactometric apparatus of this invention provides correct amounts of instillation corresponding to the different time intervals at which instilled drops fall, eliminating the possibility of errors occurring in measuring an amount of instillation. Therefore, the stactometric apparatus of the invention proves most effective the recognition of a patient's physiological condition and the application of a medical treatment. Further, the stactomatric apparatus of the invention may be provided with means for compensating for an instillation amount stored in the ROM in accordance with the viscosity of a coeliac liquid or medicinal solution being measured.

What is claimed is:
1. A stactometric apparatus comprising:
instilled drop-detecting means for generating a signal each time an instilled drop falls;
a counter coupled to said instilled drop-detecting means for measuring a time interval between falling instilled drops in response to output signals from said instilled drop-detecting means;
memory means having a plurality of memory addresses at which are respectively stored a plurality of drop volume data representing different vol- umes of drops corresponding to different time intervals between falling instilled drops;

reading means coupled to said memory means and to said counter for reading out the drop volume data from a memory address of said memory means which is specified by the contents of said counter;

moving average measuring means coupled to said memory means for measuring a moving average of at least the drop volume data successively read out by said reading means; and a display device coupled to said moving average measuring means for displaying the moving average of the drop volume data which has been measured by said moving average measuring means.

2. The stactometric apparatus of claim 1, further comprising an accumulator for successively summing the drop volume data read out of said memory means.

3. The stactometric apparatus of claim 2, further comprising a drop volume display device coupled to said accumulator to display the amount of the drop volumes successively summed thereby.

4. The stactometric apparatus of claim 1, wherein said moving average measuring means comprises:

a random access memory (RAM) having a plurality of specified addresses for storing the drop volume data successively read out of said memory means in said specified addresses of said RAM; and means coupled to said RAM for reading out the total volume of a prescribed number of falling instilled drops from said RAM, each time data on the latest instilled drop is stored therein and for determining a moving average of the amount of volumes of the prescribed number of falling instilled drops for each reading cycle.

5. A stactometric apparatus comprising:

urine drop-detecting means adapted to be coupled to a urethral catheter and arranged to generate an output signal each time a drop of coeliac urine of a human body falls;

a counter connected to said urine drop-detecting means for measuring a time interval between falling coeliac urine drops in response to output signals from said urine drop-detecting means;

a first memory having a plurality of memory addresses at which are respectively stored a plurality of urine drop volume data representing different urine drop volumes corresponding to different time intervals between falling urine drops;

reading means coupled to said first memory and to said counter for reading out the urine drop volume data from a memory address of said first memory which is specified by the count contents of said counter;

a weight data input means for producing weight data representing a weight of the human body;

a divider coupled to said weight data input means and to said first memory for calculating a urine drop volume per unit weight of the human body from the weight data and the urine drop volume data;

a second memory coupled to said divider for storing data representing the urine drop volume per unit weight;

second reading means coupled to said second memory for reading out a predetermined number of successive data representing urine drop volume per weight from said second memory, each time the latest data on the urine drop volume per weight is stored into said second memory;

calculating means coupled to said second reading means for calculating a moving average of the urine drop volumes from said successive data of urine drop volume per weight; and a display device coupled to said calculating means for displaying the moving average of urine drop volume.

6. The stactometric apparatus of claim 5, further comprising a counter for summing the urine drop volume data read out of said first memory to determine the total amount of urine drops collected for a given length of time.

7. The stactometric apparatus of claim 5, wherein said first memory is a read only memory (ROM), and said second memory is a random access memory (RAM).

8. A stactometric apparatus comprising:

a medicinal solution feed pump for instilling a medicinal solution into a human body;

an instilled drop-detector coupled to said medicinal solution feed pump and arranged to generate an output signal each time a drop of instilled medicinal solution falls;

a first counter coupled to said instilled drop-detector for measuring a time interval between the instilled medicinal solution drops in response to the output signals from said instilled drop-detector;

memory means having a plurality of memory addresses at which are respectively stored a plurality of drop volume data representing different volumes of instilled medicinal solution drops corresponding to different time intervals between the falling of instilled medicinal solution drops;

reading means coupled to said memory means and to said first counter for reading out drop data from a memory address of said memory means which is specified by the count contents of said first counter;

comparison means coupled to said memory means for comparing the drop data read out from said memory means and a predetermined volume of the instilled medicinal solution to determine the excess or deficiency of a volume of actually instilled medicinal solution and for generating an output signal showing the result of said comparison;

a second counter coupled to said memory means for counting drop data read out from said memory means;

a display device coupled to said second counter for displaying the count contents of said second counter; and means for coupling said output signal of said comparison means to said medicinal solution feed pump for controlling said medicinal solution feed pump as a function of said output signal of said comparison means to feed a proper amount of the medicinal solution to the human body.

* * * * *

UNITED STATES PATENT AND TRADEMARK OFFICE
CERTIFICATE OF CORRECTION

PATENT NO. : 4,286,590

DATED : September 1, 1981

INVENTOR(S) : Masakazu MURASE

It is certified that error appears in the above—identified patent and that said Letters Patent is hereby corrected as shown below:

COLUMN 6, line 38, after "determined is" insert --counted--.

Signed and Sealed this

Twelfth Day of January 1982

[SEAL]

Attest:

Attesting Officer

GERALD J. MOSSINGHOFF

Commissioner of Patents and Trademarks